(12) United States Patent
Veronesi et al.

(10) Patent No.: US 8,968,410 B2
(45) Date of Patent: Mar. 3, 2015

(54) GLENOID SUPPORT FOR SHOULDER PROSTHESIS

(75) Inventors: Emanuela Veronesi, Spilimbergo (IT); Piero Budassi, Cremona (IT)

(73) Assignee: Limacorporate SpA, San Daniele del Friuli (IT)

( * ) Notice: Subject to any disclaimer, the term of this patent is extended or adjusted under 35 U.S.C. 154(b) by 0 days.

(21) Appl. No.: 13/577,533

(22) PCT Filed: Feb. 10, 2011

(86) PCT No.: PCT/IB2011/000222
§ 371 (c)(1),
(2), (4) Date: Nov. 27, 2012

(87) PCT Pub. No.: WO2011/098890
PCT Pub. Date: Aug. 18, 2011

(65) Prior Publication Data
US 2013/0066433 A1   Mar. 14, 2013

(30) Foreign Application Priority Data
Feb. 10, 2010   (IT) .............................. UD2010A0024

(51) Int. Cl.
*A61F 2/40*   (2006.01)
*A61B 17/86*  (2006.01)
*A61F 2/30*   (2006.01)

(52) U.S. Cl.
CPC ....... *A61F 2/4081* (2013.01); *A61F 2002/4088* (2013.01); *A61B 17/86* (2013.01); *A61F 2/30749* (2013.01); *A61F 2002/30332* (2013.01); *A61F 2002/30433* (2013.01); *A61F 2002/30507* (2013.01); *A61F 2002/30607* (2013.01); *A61F 2002/30738* (2013.01); *A61F 2002/30878* (2013.01); *A61F 2002/30884* (2013.01); *A61F 2002/4085* (2013.01);
(Continued)

(58) Field of Classification Search
CPC . A61F 2/4081; A61F 2/40; A61F 2002/4081; A61F 2002/4085; A61F 2002/4088
USPC ................................. 623/19.13, 19.11, 19.12
See application file for complete search history.

(56) References Cited

U.S. PATENT DOCUMENTS 6,406,495 B1   6/2002   Schoch
6,953,478 B2  10/2005   Bouttens et al.
(Continued)

FOREIGN PATENT DOCUMENTS

EP   0664108   7/1995
EP   1472999   11/2004
(Continued)

OTHER PUBLICATIONS

International Search Report filed Jun. 6, 2011 for PCT/IB2011/000222.

*Primary Examiner* — David H Willse
*Assistant Examiner* — Javier Blanco
(74) *Attorney, Agent, or Firm* — Rankin, Hill & Clark LLP

(57) ABSTRACT

A glenoid support for shoulder prostheses, able to be applied to the glenoid cavity of a shoulder blade. The glenoid support includes at least an attachment plate, an anchoring pin, and a glenoid articulation element. The attachment plate and the anchoring pin are made in distinct parts and able to be selectively separated from each other.

6 Claims, 4 Drawing Sheets

(52) U.S. Cl.
 CPC *A61F 2220/0008* (2013.01); *A61F 2220/0025* (2013.01); *A61F 2220/0033* (2013.01); *A61F 2220/0041* (2013.01); *A61F 2250/0062* (2013.01)
 USPC ..................................................... 623/19.13

(56) References Cited

U.S. PATENT DOCUMENTS

2004/0220673 A1   11/2004   Pria
2007/0100458 A1*  5/2007   Dalla Pria .................. 623/19.13
2007/0173945 A1*  7/2007   Wiley et al. ................ 623/19.13

FOREIGN PATENT DOCUMENTS

| EP | 1656910 | 5/2006 |
| EP | 1782764 | 5/2007 |
| FR | 2579454 | 10/1986 |
| WO | 01/47442 | 7/2001 |
| WO | 2008/015724 | 2/2008 |

* cited by examiner

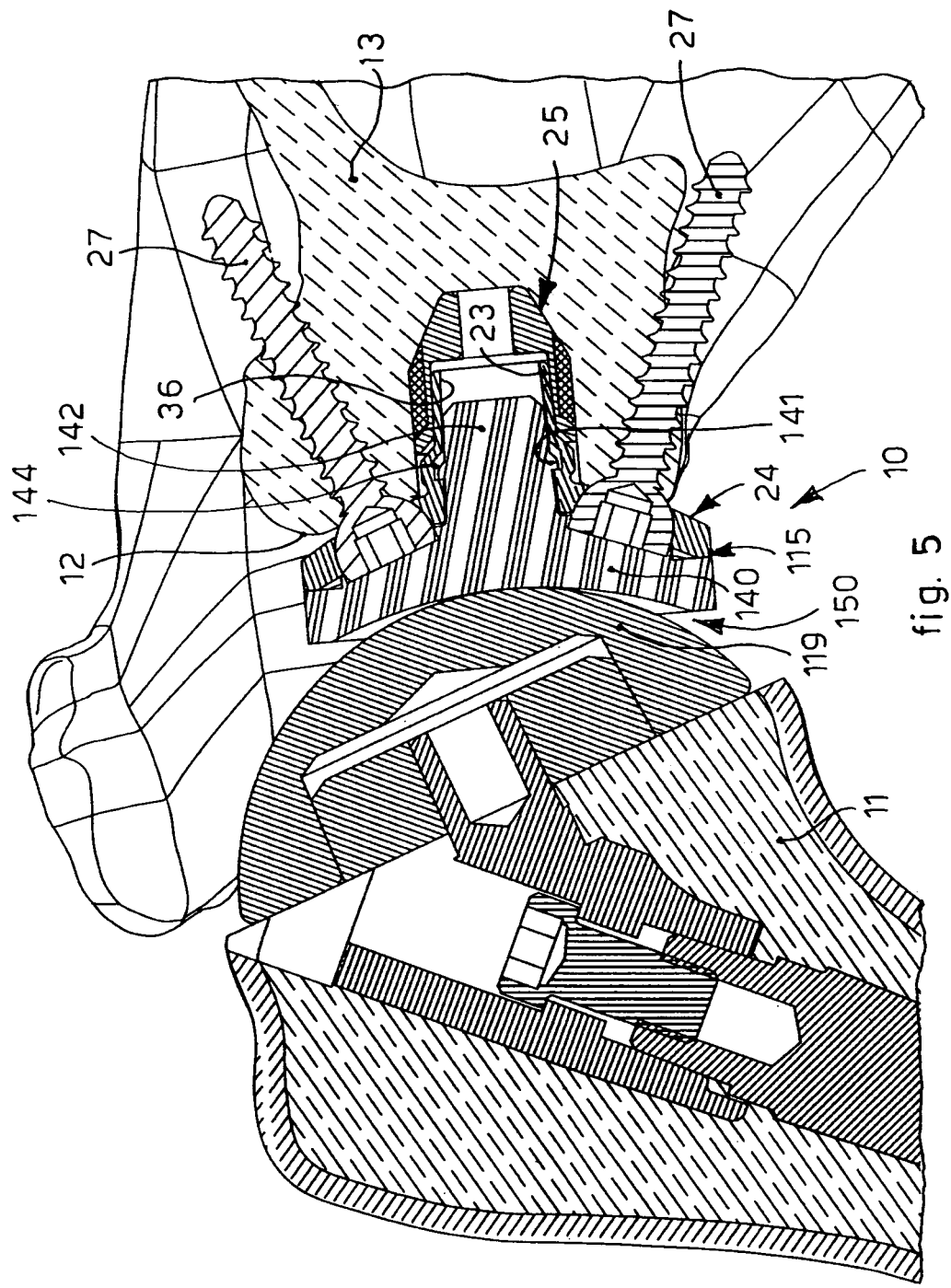

GLENOID SUPPORT FOR SHOULDER PROSTHESIS

FIELD OF THE INVENTION

The present invention concerns a glenoid element for shoulder prostheses, in particular able to be used to define at least part of an inverse prosthesis, or an anatomical prosthesis, and to be applied to the glenoid cavity of a shoulder.

The invention is applied in the medical field of the implantation of orthopedic bone prostheses.

BACKGROUND OF THE INVENTION

Shoulder prostheses are known, which comprise glenoid supports that are attached in the glenoid bone seating of the shoulder blade and allow attachment and anchorage to a shoulder blade, depending on whether it is an inverse or anatomical prosthesis, either a convex glenoid head, or a cup or a concave glenoid insert.

Known glenoid supports normally comprise a substantially flat, or at most slightly concave, attachment plate normally quadrangular or polygonal, comprising in a single piece an anchoring element, mainly cylindrical in shape, able to be attached in a corresponding seating provided in the glenoid cavity itself.

The anchoring element and/or the attachment plate can be provided with surface elements (or linings) able to promote the process of osteo-integration and to allow a greater stability of attachment inside the seating.

The attachment plate can be provided with holes to attach it to the bone using screws.

The shape and sizes of the glenoid support, and hence of the attachment plate and the anchoring element, must be chosen by the surgeon according to the particular bone conformity of the shoulder blade in which the glenoid support is to be applied, in order to optimize the implant operations and to promote the process of osteo-integration.

This implies that different glenoid supports must be prepared and made available for the surgeon, having different shapes and sizes of the attachment plate and the anchoring element, which are chosen on each occasion by the surgeon.

Furthermore, even when the condition of the bone is substantially normal, it may be difficult for the surgeon, given the extremely limited space available and the bulk of the attachment plate, to intervene with the appropriate surgical instruments in order to position and attach the whole glenoid support inside the shoulder blade precisely.

Another disadvantage of known solutions is when the prosthesis has to be checked, or when a prosthesis that was originally anatomical must be replaced by an inverse prosthesis, or vice versa, due to the difficulty of removing from the bone seating the connection between the glenoid support and the relative articulation element, whether it is concave or convex, depending on the case.

Document FR-A-2.579.454, on which the preamble to the main claim is based, shows a glenoid support in which the anchoring element and the relative plate are made in two different parts: the anchoring element has an axial cavity and is threaded externally to be attached by screwing into a bone seating already prepared, and the plate is made in two parts which can be made solid with each other using screws, and is anchored outside the neck of the shoulder blade by means of flanges that allow attachment screws to be inserted.

This solution only concerns prostheses of the anatomical type, and has an anchoring and assembly configuration that in practice renders the glenoid elements difficult to remove and/or replace without intervening very invasively on the bone part on which they are anchored.

One purpose of the present invention is to achieve a glenoid element that allows the surgeon, during the implant operations, an easy and precise positioning and correct attachment of the glenoid support in a suitable seating made in the shoulder blade.

Another purpose of the present invention is to facilitate the primary attachment of the component and its subsequent oste-integration by means of suitable fastening means suitably made on the surface of the plate and/or the anchoring element.

Another purpose of the present invention is to make a glenoid support of the modular type, which facilitates the choice of the attachment plate and also the type of anchoring element to be applied to the shoulder blade, both according to the particular bone conformation of the shoulder blade, and also the type of prosthesis to be applied, for example anatomical or inverse.

This modularity also facilitates checking the component, making it easier, less invasive and allowing the possibility of choosing the size and type of the plate and the anchoring element also in the event of a second implant.

A further purpose of the present invention is to optimize the working times and processes of the glenoid support, achieving dedicated production lines for the common workings of at least one of its parts.

Another purpose of the present invention is to achieve a glenoid support simply and economically, without in any way affecting the correct functioning of the prosthesis in its entirety.

Another purpose is to facilitate the removability and replaceability of the components, and also to allow the possibility of passing from a prosthesis of the anatomical type to one of the inverse type, or vice versa, without requiring particularly invasive interventions on the bone part of the glenoid cavity where the prosthesis is positioned.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purposes, a glenoid element for shoulder prostheses according to the invention comprises a glenoid support and a relative articulation element which, depending on the case, can be of the concave or convex type, according to whether the prosthesis is the anatomical or inverse type.

The glenoid support is able to be inserted and attached in the glenoid cavity of the shoulder blade, and comprises at least an attachment plate, normally square, rectangular or generally polygonal in shape (although it can have any shape), and an anchoring element of the pin type.

According to a first characteristic, the attachment plate and the anchoring element are made in different parts and are selectively separable from each other.

Both the anchoring element and the attachment plate have a through axial cavity which allows, if it is necessary, as will be seen hereafter, the through insertion of an anchoring element for at least a glenoid articulation element of the convex type.

In one form of embodiment, the attachment plate comprises a centering element which is at least partly inserted into the axial cavity of the anchoring element so as to achieve the reciprocal coupling after the anchoring element has already been inserted and clamped in position in the relative glenoid seating.

In order to allow a stable and precise attachment to the anchoring element, the centering element made in a single piece with the plate is substantially truncated cone shaped.

In the same way, the anchoring element is provided with a truncated cone axial cavity, having a conicity mating with that of the centering element, and able to couple therewith in order to achieve an axial alignment of the centering element and the anchoring element.

In one form of embodiment, the attachment plate comprises holes able to accommodate screws, the function of which is to increase the attachment of the glenoid support to the bone with respect to the anchoring already determined by the insertion of the anchoring element.

According to a variant, the anchoring element has surface elements able to promote the process of osteo-integration and to allow a more stable attachment of the glenoid support in the glenoid cavity.

In another form of embodiment, the attachment plate has surface elements able to promote the process of osteo-integration and to allow a more stable attachment of the glenoid support in the glenoid cavity.

In one form of embodiment of the invention, the surface elements are fins or trabecular structures.

A glenoid articulation element of the shoulder prosthesis is associated with the glenoid support, so as to constitute the glenoid element according to the invention in its entirety.

If the shoulder prosthesis is of the inverse type, the articulation element consists of a convex glenoid head which comprises a through axial hole: the hole, in use, is aligned with the through axial holes of the attachment plate and the anchoring element so as to allow the insertion of an attachment screw which makes the convex articulation element and the glenoid support solid with each other.

If the shoulder prosthesis is of the anatomical type, in the axial cavity of the attachment plate there are means that allow a coupling and stable attachment of a cup or concave insert, defining the concave glenoid articulation element of an anatomical prosthesis, and the glenoid support, so as to render the two elements solid with each other.

From the above description, it can be seen how the separability of the two components of the glenoid support, plate and anchoring element, together with their anchoring characteristics both to the glenoid bone seating and to each other, allows to optimize the characteristics and to choose, on each occasion, the most suitable components according to the bone conformation of the patient, its conditions and the type of prosthesis to be used.

For example, if it is necessary to check an anatomical prosthesis and replace it by an inverse prosthesis, it may be sufficient to remove only the concave articulation element, possibly replacing the plate with one that is more suitable for the subsequent coupling, and to apply a convex articulation element, exploiting the through axial cavity of the plate and that of the anchoring element so as to achieve the assembly, without intervening in any way on the anchoring element attached in the bone seating.

In the same way, to pass from an inverse prosthesis to an anatomical prosthesis, the screw attaching the convex articulation element to the glenoid support is removed, the plate is replaced if necessary with one more suitable to the new type of prosthesis, and then the concave articulation element is applied, using the attachment means present in the axial cavity of the plate.

In the same way, if the prosthesis has to be checked, it is simple to remove only the convex articulation element and possibly the attachment plate, leaving the anchoring element in position, without particularly invasive interventions on the bone seating, since the plate does not have bone anchoring means, in particular on the external part of the shoulder blade, which are particularly complex to remove.

BRIEF DESCRIPTION OF THE DRAWINGS

These and other characteristics of the present invention will become apparent from the following description of a preferential form of embodiment, given as a non-restrictive example with reference to the attached drawings wherein:

FIG. 5 is a longitudinal section of an anatomical prosthesis, implanted in a shoulder, using a glenoid element according to the present invention.

Figure 1:
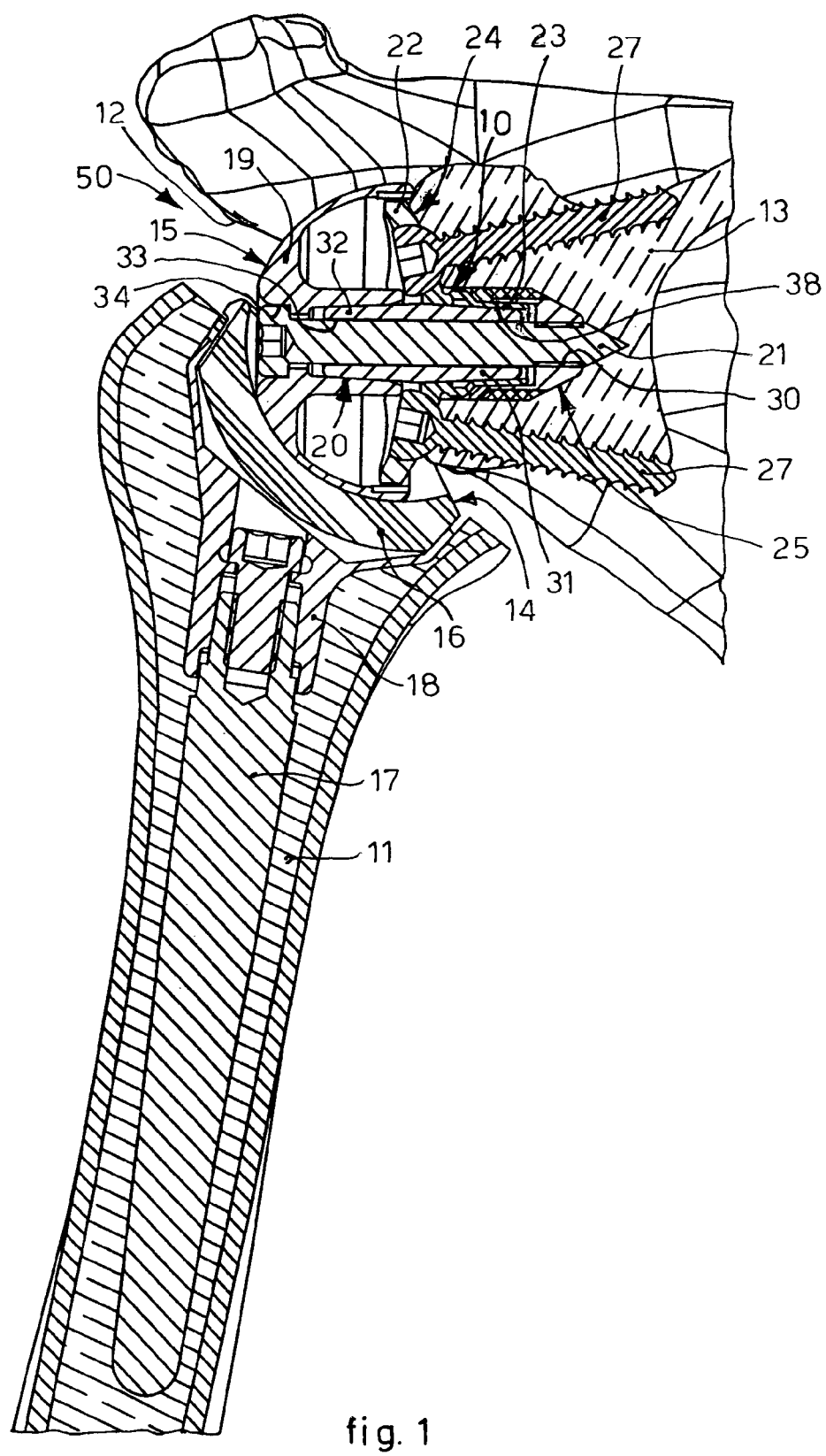
FIG. 1 is a longitudinal section of an inverse prosthesis, implanted in a shoulder, using a glenoid element according to the present invention.

To facilitate comprehension, the same reference numbers have been used, where possible, to identify common elements in the drawings that are substantially identical. It is understood that elements and characteristics of one form of embodiment can conveniently be incorporated into other forms of embodiment without further clarifications.

DETAILED DESCRIPTION OF SOME PREFERENTIAL FORMS OF EMBODIMENT

Figure 4:
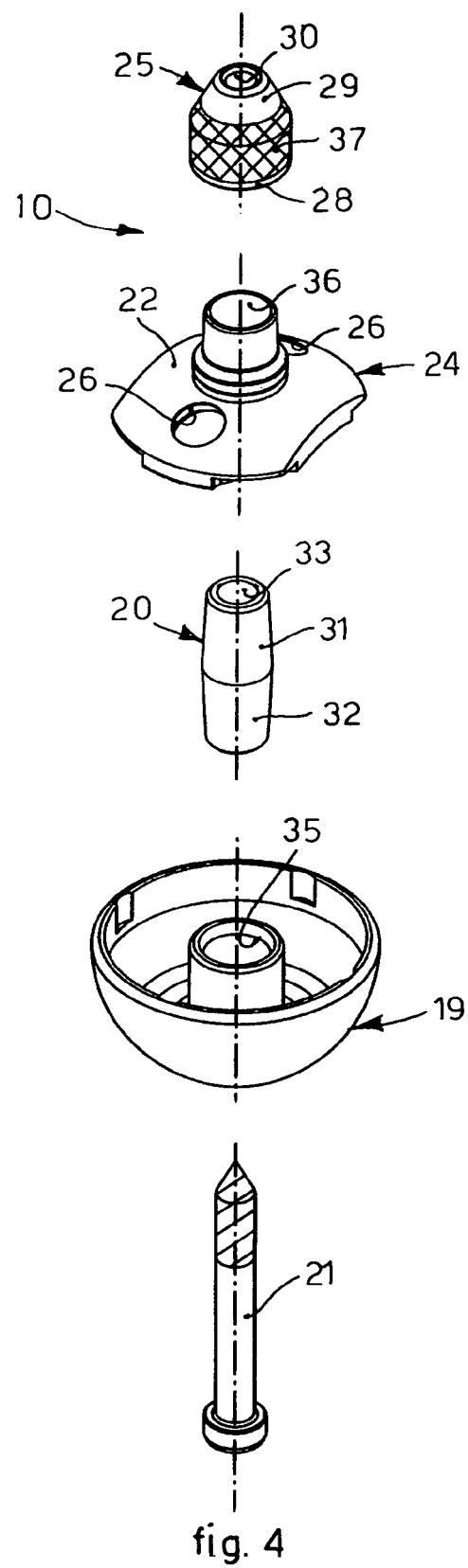
FIG. 4 is an exploded view of a variant of a detail of FIG. 1.

With reference to FIGS. 1 and 4, a glenoid support 10 is associated with an inverse prosthesis 50 implanted in a shoulder and comprises an attachment plate 24 and an associated anchoring element or pin 25, made in separate parts from each other.

The inverse prosthesis 50 allows the articulation of a humerus 11 in a relative glenoid cavity 12 of a shoulder blade 13.

In particular, the inverse prosthesis 50 comprises a first articulation element 14 associated with the humerus 11 and a second articulation element or glenosphere 15 associated with the shoulder blade 13.

The first articulation element 14 in turn comprises a humeral cup, also called humeral body 16, a rod 17 able to be inserted into the humerus 11, and a coupling cone 18 which allows to attach and position the humeral body 16 in the rod 17. Inside the humeral body 16 an insert is housed, intended for coupling with the glenosphere 15.

The glenosphere 15 comprises a glenoid head 19, of the hemispheric type, and a bushing 20.

The bushing 20 and the glenoid head 19 are coupled with the glenoid support 10 with an attachment screw 21, which passes entirely through the through axial cavities or holes 36, 38, and 30 made respectively the first in the attachment plate 24 and the second two in the anchoring pin 25.

In a variant, not shown in the drawings, the bushing 20 is coupled with the glenoid support 10 by means of a suitable adaptor cone and an attachment screw.

The attachment plate 24 in this case comprises a base body 22, substantially square or rectangular in shape, and a centering element 23 made in a single piece between them.

The base body 22 has a slightly concave shape, so that it can adapt better to the shape of the glenoid cavity 12, and is provided with two holes 26 into which screws 27 can be inserted, which screw into the bone part of the shoulder blade 13.

The base body 22 can have any shape and sizes, which are chosen on each occasion by the surgeon in relation to the particular bone conformation of the shoulder blade 13, the specific conditions in which he has to operate, and the type of prosthesis to be applied.

Figure 3:
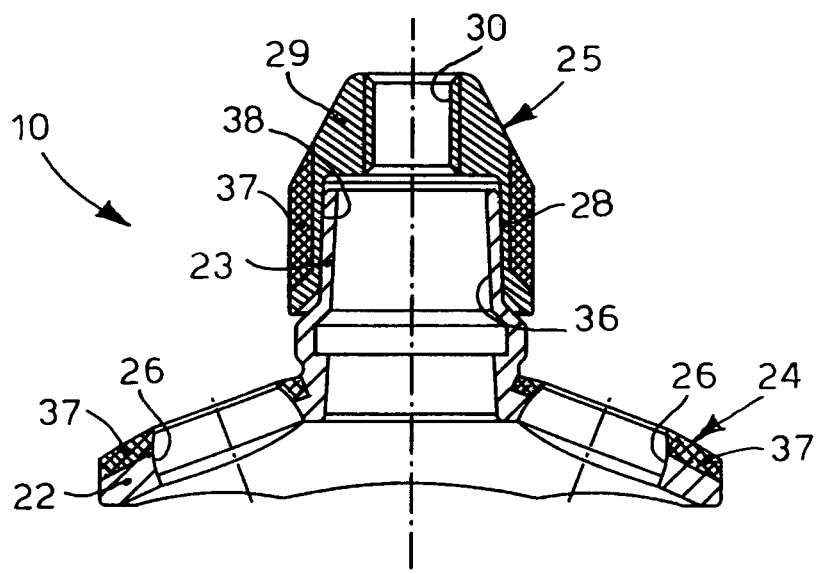

In some forms of embodiment, for example with reference to FIG. 3, the base body 22 can be provided, on the surface that goes into contact with the bone, with surface elements 37, such as trabecular or porous structures, able to promote the process of osteo-integration and to make the bone solid with the attachment plate 24.

The centering element 23 is substantially cylindrical in shape, preferably truncated cone, flared toward the outside, and is provided internally with the through axial cavity 36, which is also slightly truncated cone shaped. The external surface of the centering element 23 is able to couple with the mating axial cavity of the anchoring pin 25, while its through cavity 36 is able to couple with the bushing 20.

The anchoring pin 25 comprises a part 28 which in use is more external with respect to the glenoid seating, substantially cylindrical, and a more internal part 29, substantially truncated cone shaped, able to promote the insertion thereof into a suitable seating made in the bone part of the shoulder blade 13.

The part 28 which is more external in use is provided with the through axial cavity 38 and with surface elements 37. The axial cavity 38 has a conicity mating with that of the centering element 23 of the plate 24, and is able to couple therewith so as to achieve an axial alignment of the attachment plate 24 and the anchoring pin 25.

According to other forms of embodiment, the surface elements 37 comprise fins, ridges, knurled surfaces or suchlike.

The shape of the surface elements 37 characterizes the single anchoring pin 25, which will be chosen by the surgeon according to the particular structure and conformation of the bone part of the shoulder blade 13.

The part 29 of the anchoring pin 25 which in use is more internal is provided with a threaded hole 30, axial and through, disposed as an extension of the truncated cone cavity 38, into which the attachment screw 21 can be screwed.

Figure 2:
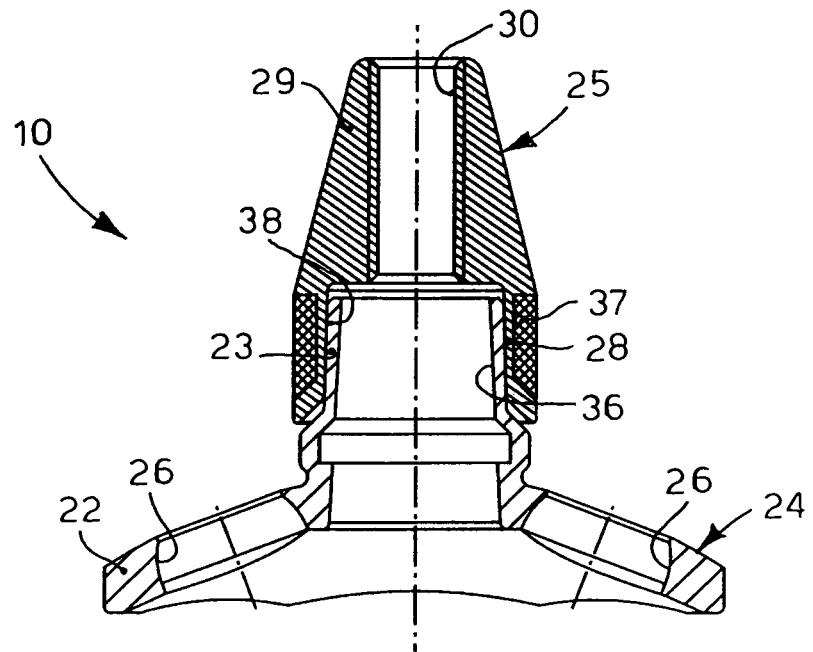
FIGS. 2 and 3 are a section of the glenoid element in FIG. 1 on an enlarged scale.

The size and shape of the anchoring pin 25 can be different according to the application required, as can be seen by comparing FIG. 2 and FIG. 3, although it can be coupled with the same attachment plate 24.

The bushing 20 comprises a part 31 which is more internal in use, and a part 32 which is more external in use, both truncated cone shaped. The internal part 31 couples in use with the through axial cavity 36 of the centering element 23 of the attachment plate 24, and the external part 32 is inserted into the glenoid head 19.

The glenoid head 19 comprises internally a through cavity 35 of a shape mating with that of the external part 32 of the bushing 20.

According to one form of embodiment, not shown in the drawings, the bushing 20 can be grafted onto the head 19 in advance, and the connection to the attachment plate 24 is made by means of a suitable through adaptor cone, able to accommodate the attachment screw 21.

The external surface of the external part 32 of the bushing 20 can be coupled through simple interference with the cavity 35 of the glenoid head 19.

The bushing 20 is also provided with a through hole 33 able to accommodate the attachment screw 21, and the glenoid head 19 is provided with a seating 34 able to accommodate the head of the attachment screw 21.

The glenoid support 10 and the glenosphere 15 are assembled as follows. First of all, the anchoring pin 25 is inserted into a suitable seating made in the bone part of the shoulder blade 13. Then the centering element 23 of the attachment plate 24 is inserted into the anchoring pin 25. In a variant, the anchoring pin 25 and the attachment plate 24 are supplied already assembled.

The attachment plate 24 is then attached to the shoulder blade 13 with the screws 27, which cause an increase in the attachment of the glenoid support 10 to the bone seating, already achieved in practice by the truncated cone shape of the anchoring pin 25.

Then the external part 32 of the bushing 20 is coupled by interference with the through cavity 35 of the glenoid head 19, and subsequently the internal part 31 of the bushing 20 is inserted inside the cavity 36 of the attachment plate 24.

The attachment screw 21 is then inserted through the seating 34 of the glenoid head 19 and into the through hole 33 of the bushing 20, then into the cavity 36 of the attachment plate 24, to be screwed into the threaded hole 30 of the anchoring pin 25, so as to attach the glenosphere 15 to the glenoid support 10 and hence to the shoulder blade 13.

The coaxiality, and hence the alignment, of the through hole 33, the seating 34, the threaded hole 30 and the attachment screw 21 is guaranteed by the truncated cone shape of the internal part 31 of the bushing 20, the centering element 23 of the attachment plate 24 and the anchoring pin 25.

With reference to FIG. 5, the glenoid support 10 according to the present invention is used to attach an articulation element 115 of a prosthesis of the anatomical type 150. In this case, the glenoid articulation element, which replaces the glenosphere 15 in the case of an inverse prosthesis as in FIG. 1, is an insert for glenoid 140, associated with the glenoid cavity 12, while the humeral articulation element consists of a glenoid head 119, able to be attached to the humerus 11.

The glenoid support 10 is substantially equivalent to the one described above in the case of an inverse prosthesis 50 and, as before, provides the anchoring pin 25 inserted and attached in the glenoid seating of the shoulder blade, and the attachment plate 24, which has holes for the screws 27 that increase the attachment to the bone of the support 10.

The insert for glenoid 140 in this case comprises a centering pin 142 which is provided, on the periphery, with one or more clamping elements 141 which anchor in one or more corresponding grooves 144 made on the internal part of the axial cavity 36 of the attachment plate 24. Thanks to this coupling, the articulation element, in this case the concave insert for glenoid 140, can be attached to the glenoid support 10 by means of the clamping element 141, inserted in the grooves 144.

From the above description it can be seen that the removability of the anchoring pin 25 and attachment plate 24 allows to select on each occasion the element most suitable for the case and for the specific type of prosthesis.

The possibility of anchoring the articulation element, whether it is a convex glenosphere 15 or a concave glenoid insert 140, to specific parts of the glenoid support 10, whether they are the through axial cavities 36, 30 in the case of a through screw 21, or the groove 144 in the case of an insert 140, allows to remove on each occasion only the parts to be replaced, without making the intervention invasive on the bone parts.

It is clear that modifications and/or additions of parts may be made to the glenoid prosthetic element as described heretofore, without departing from the field and scope of the present invention.

The invention claimed is:

1. A glenoid element for a shoulder prosthesis, able to be inserted in the glenoid cavity (12) of a shoulder blade (13), said glenoid element comprising:
   a glenosphere (15) configured to articulate with a mating humeral articulation element, said glenosphere comprising glenoid head (19) having a hemispherical articulation surface and a through axial hole;
   a discrete bushing (20);
   an attachment screw (21); and
   a glenoid support (10) configured to be inserted in the glenoid cavity, said glenoid support comprising:
      an attachment plate (24) comprising a generally polygonal base body (22) having a slightly concave shape, a substantially cylindrical centering element (23) made in a single piece with the base body, and through holes (26) provided in the base body for the insertion of screws (27) to anchor the base body to the bone of said shoulder blade, wherein the attachment plate further comprises a through axial cavity (36) extending through the base body and centering element, and wherein the through holes are positioned in the base body such that the screws inserted into the through holes are angled away from the centering element; and
      a discrete anchoring pin (25) that is made separate with respect to the attachment plate and is selectively able to be coupled with/separated from said attachment plate, wherein the anchoring pin comprises a substantially cylindrical part (28) having a first through axial cavity (38) and a substantially truncated cone shaped part (29) having a second through axial cavity (30),
   wherein said centering element of the attachment plate and said first through axial cavity of the anchoring pin have a mating truncated cone shape, and said centering element is inserted in said first through axial cavity in order to couple said attachment plate to said anchoring pin,
   wherein an end of said bushing is inserted in said through axial cavity of the attachment plate, and an opposite end of said bushing is coupled to said glenosphere,
   wherein said attachment screw is inserted through the glenosphere, through the bushing, through the attachment plate, and screwed into said second through axial cavity of the anchoring pin to achieve a stable connection of said glenosphere with said glenoid support.

2. The glenoid element as in claim 1, wherein said anchoring pin includes surface elements able to promote the process of osteo-integration and to allow a more stable attachment of the glenoid support in the glenoid cavity.

3. The glenoid element as in claim 1, wherein said attachment plate has surface elements able to promote the process of osteo-integration and to allow a more stable attachment of the glenoid support in the glenoid cavity.

4. A glenoid element for a shoulder prosthesis, able to be inserted in the glenoid cavity (12) of a shoulder blade (13), said glenoid element comprising:
   a concave insert for glenoid (140) associated with the glenoid cavity (12);
   a glenoid head (119) able to be attached to an humerus (11);
   a glenoid support (10) configured to be inserted in the glenoid cavity, said glenoid support comprising:
      an attachment plate (24) comprising a generally polygonal base body (22) having a slightly concave shape, a substantially cylindrical centering element (23) made in a single piece with the base body, and through holes (26) provided in the base body for the insertion of screws (27) to anchor the base body to the bone of said shoulder blade, wherein the attachment plate further comprises a through axial cavity (36) extending through the base body and centering element, and wherein the through holes are positioned in the base body such that the screws inserted into the through holes are angled away from the centering element; and
      a discrete anchoring pin (25) that is made separate with respect to the attachment plate and is selectively able to be coupled with/separated from said attachment plate, wherein the anchoring pin comprises a substantially cylindrical part (28) having a first through axial cavity (38) and a substantially truncated cone shaped part (29) having a second through axial cavity (30),
   wherein said centering element of the attachment plate and said first through axial cavity of the anchoring pin have a mating truncated cone shape, and said centering element is inserted in said first through axial cavity in order to couple said attachment plate to said anchoring pin,
   wherein the insert for glenoid (140) comprises a centering pin (142) provided on the periphery with one or more clamping elements (141) which anchor in one or more corresponding grooves (144) made on the internal part of the axial cavity (36) of the attachment plate (24) to achieve a stable connection of said concave insert for glenoid with said glenoid support.

5. The glenoid element as in claim 4, wherein said anchoring pin includes surface elements able to promote the process of osteo-integration and to allow a more stable attachment of the glenoid support in the glenoid cavity.

6. The glenoid element as in claim 4, wherein said attachment plate has surface elements able to promote the process of osteo-integration and to allow a more stable attachment of the glenoid support in the glenoid cavity.

* * * * *